US010238942B2

United States Patent
Dalton

(10) Patent No.: US 10,238,942 B2
(45) Date of Patent: Mar. 26, 2019

(54) SNOWBOARD TRAINER

(71) Applicant: David Dalton, Liberty, UT (US)

(72) Inventor: David Dalton, Liberty, UT (US)

( * ) Notice: Subject to any disclaimer, the term of this patent is extended or adjusted under 35 U.S.C. 154(b) by 0 days.

(21) Appl. No.: 15/521,235

(22) PCT Filed: Jun. 16, 2016

(86) PCT No.: PCT/US2016/037791
§ 371 (c)(1),
(2) Date: Apr. 21, 2017

(87) PCT Pub. No.: WO2016/205463
PCT Pub. Date: Dec. 22, 2016

(65) Prior Publication Data
US 2018/0085650 A1    Mar. 29, 2018

Related U.S. Application Data

(60) Provisional application No. 62/180,213, filed on Jun. 16, 2015.

(51) Int. Cl.
*A63B 24/00* (2006.01)
*A63B 26/00* (2006.01)
(Continued)

(52) U.S. Cl.
CPC ........ *A63B 69/0093* (2013.01); *A63F 13/211* (2014.09); *A63F 13/245* (2014.09);
(Continued)

(58) Field of Classification Search
CPC .... A63F 13/428; A63F 13/211; A63F 13/807; A63F 13/245; A63C 5/03;
(Continued)

(56) References Cited

U.S. PATENT DOCUMENTS 5,192,258 A * 3/1993 Keller ................... A63B 69/18
434/253
5,895,340 A    4/1999 Keller

FOREIGN PATENT DOCUMENTS

AT     204939 B     8/1959
CN     202128876 U  2/2012
(Continued)

*Primary Examiner* — Gene Kim
*Assistant Examiner* — Jeffrey Vanderveen
(74) *Attorney, Agent, or Firm* — Maschoff Brennan

(57) ABSTRACT

A snowboard trainer (SBT) includes an SBT platform, a slide rail, slide supports, a central stand, and a front interface. The slide rail extends from a first end to a second end. The slide supports connect the slide rail to the SBT platform. The slide supports are configured to support the slide rail relative to the SBT platform. The central stand is positioned relative to the slide rail on the SBT platform and positioned between the first end and the second end of the slide rail. The central board receiver is connected to the central stand. The front interface is configured to be secured to a front portion of a snowboard. The front interface includes a roller bearing sized to be retained in the central board receiver such that when the roller bearing is received in the central board receiver, the front interface three-dimensionally rotates relative to the central stand.

18 Claims, 9 Drawing Sheets

(51) Int. Cl.
  *A63B 69/00* (2006.01)
  *A63B 71/06* (2006.01)
  *A63C 5/03* (2006.01)
  *A63F 13/211* (2014.01)
  *A63F 13/245* (2014.01)
  *A63F 13/428* (2014.01)
  *A63F 13/807* (2014.01)

(52) U.S. Cl.
  CPC .......... *A63F 13/428* (2014.09); *A63F 13/807* (2014.09); *A63B 26/003* (2013.01); *A63B 69/0064* (2013.01); *A63B 71/0622* (2013.01); *A63B 2024/0096* (2013.01); *A63B 2071/0625* (2013.01); *A63B 2220/13* (2013.01); *A63B 2220/808* (2013.01); *A63B 2225/093* (2013.01); *A63B 2225/50* (2013.01); *A63C 5/03* (2013.01)

(58) Field of Classification Search
  CPC ............ A63B 69/0093; A63B 69/0064; A63B 2225/50; A63B 2071/0625; A63B 2024/0096; A63B 26/003; A63B 71/0622; A63B 2220/808
  See application file for complete search history.

(56) References Cited

FOREIGN PATENT DOCUMENTS

| | | |
|---|---|---|
| DE | 202004000864 U1 | 4/2004 |
| JP | 2001149518 A | 6/2001 |

* cited by examiner

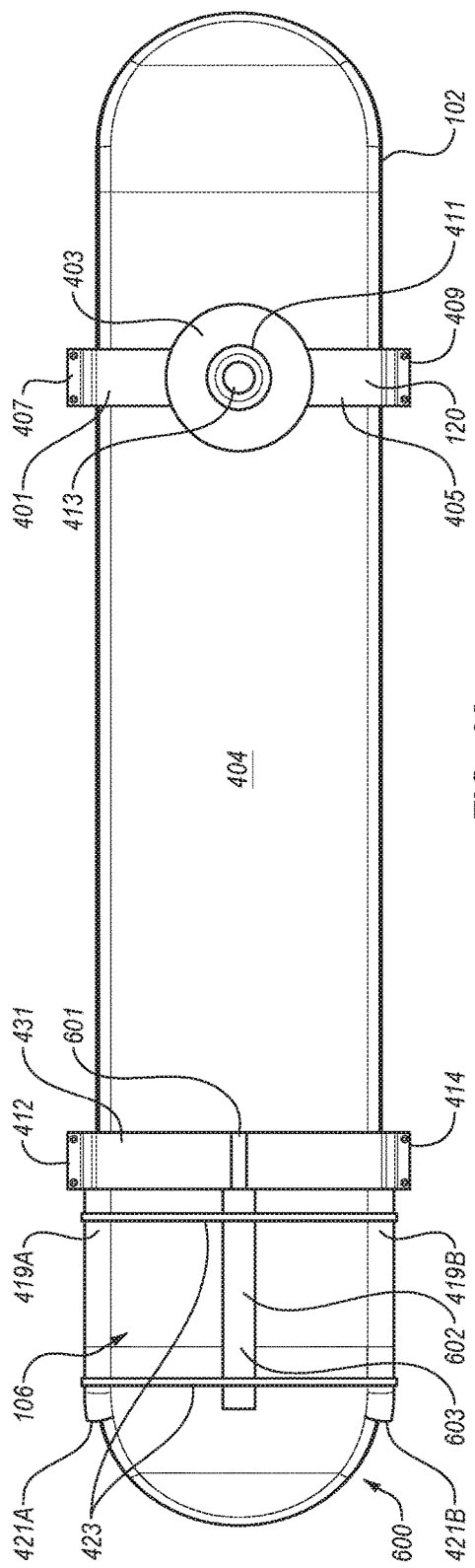
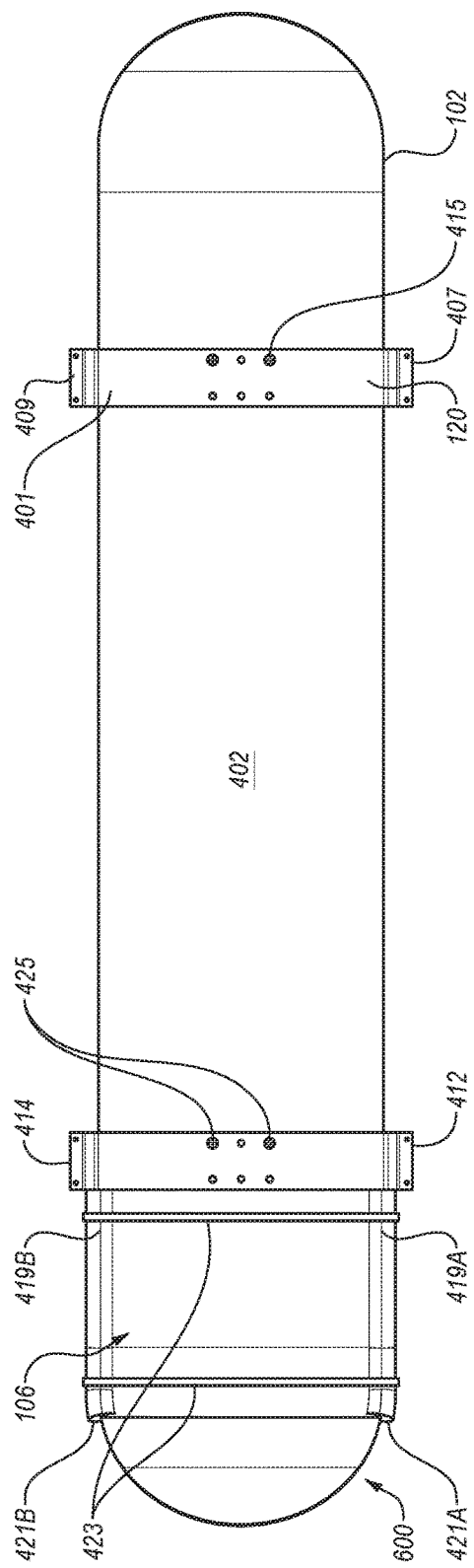
FIG. 4A
FIG. 4B

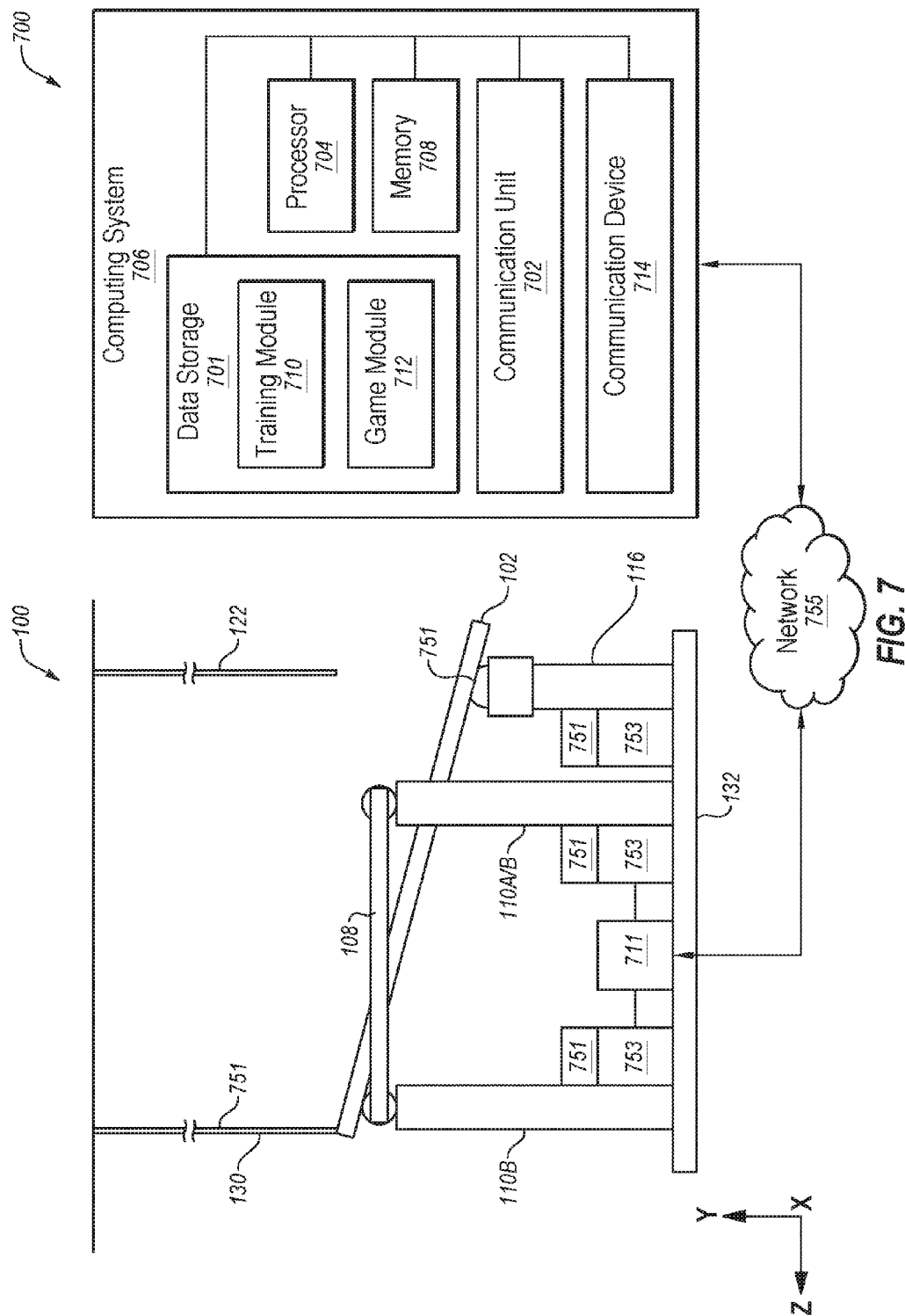

SNOWBOARD TRAINER

RELATED APPLICATION

This application claims benefit of and priority to U.S. Prov. App. No. 62/180,213 filed Jun. 16, 2015, which is incorporated herein by reference in its entirety.

FIELD

Embodiments described in this disclosure relate to snowboard trainers.

BACKGROUND

Snowboarding can be a fun and enjoyable sport; however the initial learning curve is steep and injuries can occur without proper practice and training. Snowboarding involves a particular muscle development and balance. Generally, this muscle development and balance is obtained while attempting to snowboard on the mountain. Most beginning snowboarders are unsuccessful during their initial attempts which can lead to frustration and injury. For example, some beginning-snowboarders repeatedly fall, which may hurt their wrists and tail bones. Additionally, many beginning snowboarders spend the first couple of days scooting down the hill rather than properly snowboarding. Moreover, snowboarding is a seasonal sport that occurs in an outdoor environment. Between winters, snowboarders can lose the progress they achieved because they have not continued to strengthen muscles involved in the sport. Thus, snowboarders can spend a few days each season regaining their proficiency. Furthermore, following an injury, rehabilitation can be difficult.

The subject matter claimed herein is not limited to embodiments that solve any disadvantages or that operate only in environments such as those described above. Rather, this background is only provided to illustrate one example technology area where some embodiments described herein may be practiced.

SUMMARY

An aspect of the present disclosure is a snowboard trainer (SBT). The SBT may include an SBT platform, a slide rail, slide supports, a central stand, and a front interface. The slide rail may extend from a first end to a second end. The slide supports may connect the slide rail to the SBT platform. The slide supports may be configured to support the slide rail relative to the SBT platform. The central stand may be positioned relative to the slide rail on the SBT platform and positioned between the first end and the second end of the slide rail. The central board receiver may be connected to the central stand. The front interface may be configured to be secured to a front portion of a snowboard. The front interface includes a roller bearing sized to be retained in the central board receiver such that when the roller bearing is received in the central board receiver, the front interface three-dimensionally rotates relative to the central stand.

The object and advantages of the embodiments will be realized and achieved at least by the elements, features, and combinations particularly pointed out in the claims. It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which:

FIG. 4A illustrates an example front interface and rear interface that may be implemented in the SBT of FIG. 1;
FIG. 4B illustrates another view of the front interface and the rear interface of FIG. 4A;
FIG. 7 illustrates a block diagram of the SBT of FIG. 1 implemented with a computing system configured for snowboard training or gaming.

DESCRIPTION OF SOME EXAMPLE EMBODIMENTS

Figure 1:
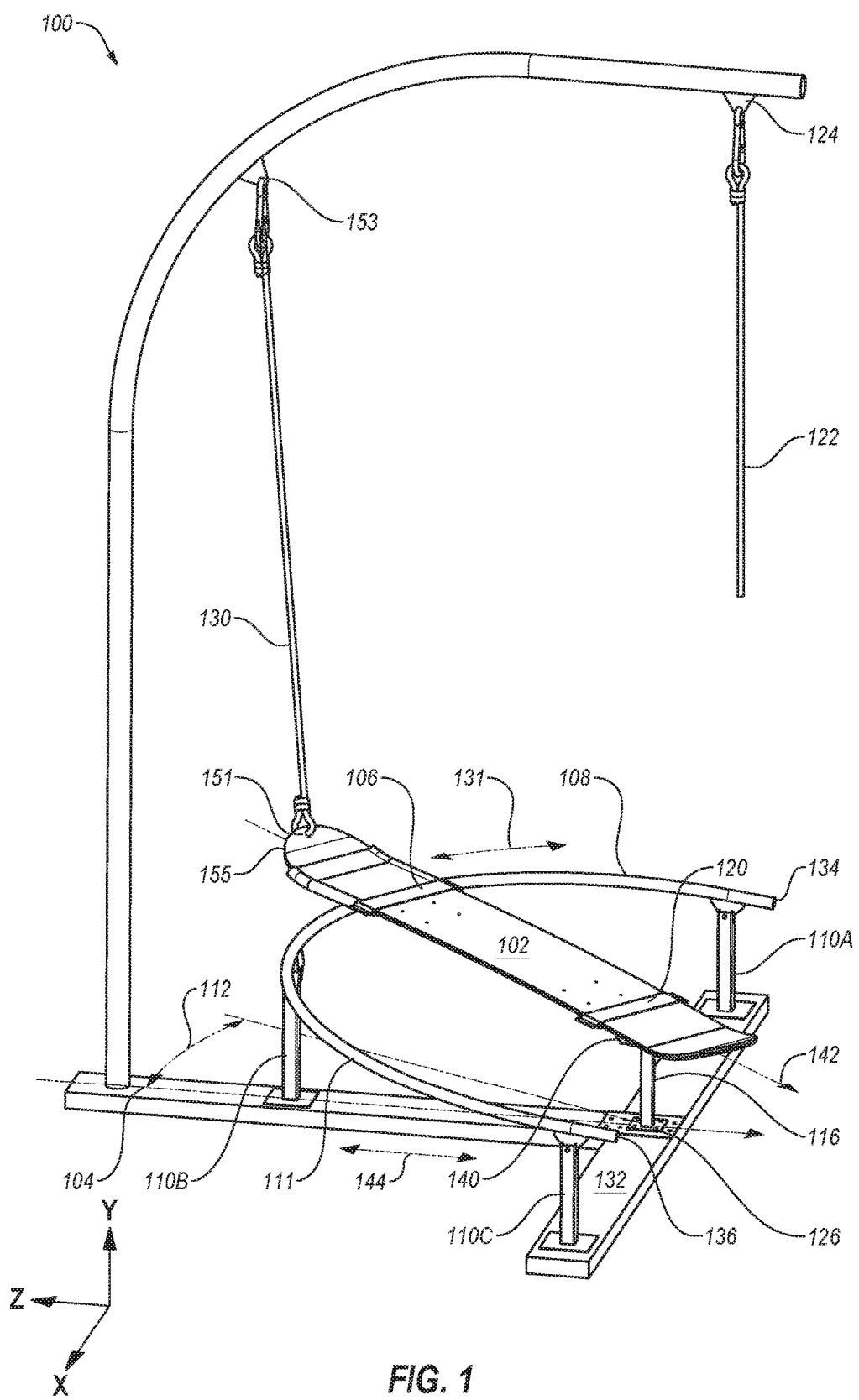
FIG. 1 illustrates an example snowboard trainer (SBT)

Snowboarding can be a fun and enjoyable sport; however the initial learning curve is steep and injuries can occur without proper practice and training. Moreover, snowboarding is a seasonal sport that occurs in an outdoor environment. Between winters, snowboarders can lose the progress they achieved because they have not continued to strengthen muscles involved in the sport. Furthermore, following an injury, rehabilitation can be difficult. Accordingly, embodiments described in this disclosure include a snowboard trainer (hereinafter, "SBT"). The SBT is configured to train snowboarders mentally and physically. For example, the SBT may be used before a beginning snowboarder attempts the sport, during an off-season, during the rehabilitation of an injury, to perfect or further develop the balance of experienced snowboarders, or some combination thereof.

For example, some embodiments include an SBT designed to assist the beginning snowboarder in learning and practicing the basic skills involved in snowboarding before they attempt the sport. These and other embodiments can be implemented by snowboarding instructors to assist them with their training. The SBT may include multiple settings, which may allow a user to advance as they achieve or develop the muscle memory, balance, and form to successfully use the device.

In particular, Professional Ski Instructors of America-American Association of Snowboard Instructors (PSIA-AASI) has developed a snowboard training program. The PSIA-AASI training program focuses on four "performance concepts" that are used in snowboarding. The four performance concepts are tilt, pivot, twist, and pressure. The tilt is "[t]he act of creating an angle between both edges or one edge and the sliding surface of the snowboard." The pivot is "[t]he act of rotating a snowboard around a particular point or axis along its length." The twist is "[t]he act of applying a torsional force that changes the mount of edge angle and pressure along the length of the snowboard." The pressure is "[t]he act of managing the degree and location of forces between the snowboard and the snow along the snowboard's length (tip to tail) and width (edge to edge)." These definitions and further discussion of these performance concepts are provided in the American Association of Snowboard Instructors, *SNOWBOARD TECHNICAL MANUAL* 45-56

(2014), which is incorporated herein by reference. Some embodiments described in this disclosure address each of these performance concepts. Moreover, through alteration of configurations of the SBT, a user may develop skill related to each of these performance concepts.

Furthermore, in some embodiments, in addition to being used for training snowboarders, the SBT may be configured to provide input to a gaming or computing system. For example, while simulating the actions involved in snowboarding, one or more sensors attached to the SBT may measure physical positions, rates of change of positions, angles, and the like. Data representative of the measured values may be communicated to a computing system. The computing system may process the data and incorporate the data in a snowboarding program or a snowboarding game.

In an example embodiment, the SBT includes a substantially C-shaped slide rail (slide rail) and a central stand that is positioned relative to the slide rail. The slide rail is configured to be selectively interfaced with a rear portion of a snowboard and/or a rear interface that is attached to the rear portion of a snowboard. Additionally, the central stand or a receiver included thereon is configured to be selectively interfaced with a front portion of the snowboard and/or a front interface that is attached to the front portion of the snowboard. The receiver on the central stand secures the snowboard relative to the central stand while enabling three-dimensional rotation of the front interface. The three-dimensional rotation of the front interface includes rotational degrees of freedom about at least two substantially perpendicular axes. During use, the slide rail interfaces with the rear portion of the snowboard or the rear interface and the central stand interfaces with the front portion of the snowboard or the front interface. The user positions herself on the snowboard and moves the snowboard relative to the SBT. Movement of the snowboard relative to the SBT simulates the performance concepts introduced above.

For example, the slide rail includes a low friction surface. The low friction surface is the surface of the slide rail that contacts the rear portion of the snowboard and/or the rear interfaces. During use of the SBT, the rear portion of a snowboard and/or the rear interface contact the low friction surface as the rear portion of a snowboard and/or the rear interfaces rotationally translate relative to the slide rail. Rotational translation of the rear portion of a snowboard and/or the rear interfaces may simulate the performance concept of pivot described in the AASI training program and the low friction surface may simulate sliding on snow.

The slide rail is supported by three vertically adjustable slide supports. One of the slide supports is at either end of the slide rail and one of the slide supports a central portion of the slide support. The height of the three slide supports can be manually, electro-mechanically, or otherwise adjusted. Changing the height of the slide supports together or separately changes an angle of the slide rail relative to a surface on which the SBT is placed (e.g., a floor of a gym). Additionally or alternatively, the changing of the height of the slide supports can change the height from the surface of the slide rail relative to a height of the central stand, which changes an angle of the snowboard during use of the SBT. Accordingly, adjustment of the slide supports may simulate a feeling of a user of various terrains that may be encountered on a mountain slope. For instance, angles of terrains can be simulated through adjustment of the slide supports.

The receiver of the central stand includes a pocket. The pocket may be configured to retain a hemispherical surface or roller bearing that is included in the front interface. The hemispherical surface or the roller bearing three-dimensionally rotates relative to the receiver, which allows the snowboard to rotationally translate relative to the slide rail and to tilt the snowboard from edge to edge. The tilt may simulate heel turns and/or toe turns involved in snowboarding.

The rear interface includes a round contact element. The round contact element is configured to contact the low friction surface of the slide rail. The round contact element elevates the snowboard from the low friction surface and enables the snowboard to rotate about an axis of the round contact element. In response, at least the rear portion of the snowboard may tilt. Furthermore, the user can rotate the rear portion in a first direction about the axis of the round contact element while tilting the front portion of the snowboard about the receiver in a second direction that is substantially opposite the first direction. Rotation of the rear portion in the first direction with rotation of the front portion in the second direction may twist the snowboard and may simulate the AASI performance concept of twist.

In addition, the user can rotate the rear portion in a first direction about the axis of the round contact element while tilting the front portion of the snowboard about the receiver in the first direction. Rotation of the rear portion and the front portion in the first direction tilts the snowboard and may simulate the AASI performance concept of tilt.

The SBT may include a return assist cord. The return assist cord is configured to attach to the rear portion of the snowboard. The return assist cord may reduce weight on the rear portion of the snowboard imposed by a user. The return assist cord may encourage the user to place more weight on the front portion of the snowboard during use of the SBT. In addition, the return assist cord may prevent the snowboard from sliding off the ends of the slide rail and may simulate a floating feeling of a rear foot of the user. The return assist cord may also help to return the snowboard to the center of the slide rail. The user may push against the return assist cord and reorient her body to return the snowboard to the center of the slide rail during use, which may simulate the AASI performance concept of pressure.

Some additional details of these and other embodiments are discussed with respect to the appended figures. The drawings are diagrammatic and schematic representations of some embodiments, and are not meant to be limiting, nor are they necessarily drawn to scale. In the drawings, like numbers generally reference like structures unless described otherwise.

FIG. 1 is a top perspective view of an example SBT 100. The SBT 100 of FIG. 1 is depicted interfaced with a snowboard 102 (hereinafter, "board"). The board 102 is selectively positioned on the SBT 100 via a front interface 120 and a rear interface 106. The board 102 is depicted some distance 112 in a first direction from a central position, which is generally indicated by datum 104.

When the board 102 is positioned on the SBT 100, the SBT 100 allows the board 102 to slide along a slide rail 108, which may result in substantially rotational displacement about a central stand 116. In FIG. 1, movement of the board 102 relative to the SBT 100 may be in directions shown by arrow 131. For example, the board 102 may slide along the slide rail 108 from a first end 134 through the central position 104 to a second end 136. Similarly, the board 102 may slide along the slide rail 108 from the second end 136 through the central position 104 to the first end 134. Additionally, the movement of the board 102 may include any portion of the slide rail 108 between the second end 136 and the first end 134.

The SBT 100 may include the slide rail 108, slide supports 110A-110C (generally, slide support 110 or slide supports 110), the central stand 116, a return assist cord 130, and an SBT platform 132.

In the depicted embodiment, the slide rail 108 may include a C-shaped configuration as viewed in the xz plane (e.g., from the top or bottom as shown in FIG. 1). The slide rail 108 extends from the first end 134 to the second end 136. In some embodiments, the slide rail 108 may include two portions, a first portion that extends from the first end 134 to a second slide support 110B and a second portion that extends from the second slide support 110B to the second end 136. The two portions may be configured such that rotation of the board 102 is smooth along an entire length of the slide rail 108. For example, the first portion of the slide rail 108 may be joined with the second portion of the slide rail 108 at the second slide support 110B such that motion of the board 102 is not interrupted. In some embodiments, the slide rail 108 may be a single structure that extends from the first end 134 to the second end 136 or may include more than two (e.g., three, four, or five) portions.

The slide rail 108 may have a circular cross section. For instance, in FIG. 1, the cross section may include a plane of the slide rail 108 that is parallel to the yz plane in the arbitrarily defined coordinate system at the second slide support 110B. In some embodiments, the cross section may be substantially constant between the first end 134 and the second end 136. In other embodiments, the slide rail 108 may have a substantially flat (e.g., planar in the xz plane) surface that contacts the rear interface 106. In some embodiments, the slide rail 108 may include another shape such as a modified C-shape, a semi-circular shape, a semi-elliptical shape, and the like.

In some embodiments, the slide rail 108 may be installed in tension. For example, the slide rail 108 may be compressed in substantially the x-direction e.g., such that the first end 134 is pressed towards the second end 136. While in compression, the slide rail 108 may be coupled or attached to the slide supports 110.

The slide rail 108 may include an outer surface 111. The outer surface 111 contacts the rear interface 106 when the board 102 is positioned on the SBT 100. The outer surface 111 may be treated, finished, painted, or otherwise conditioned such that it is a low friction surface. Low friction as used in this disclosure to describe the outer surface 111 of the slide rail 108 may include a surface that has a kinetic coefficient of friction that is sufficient to enable the rear interface 106 to slide along the slide rail 108 with minimal resistance. Example coefficients of friction may be in a range of about 0.04 to about 0.3. In some embodiments only a portion of the outer surface 111 may be conditioned to be low friction. For example, in some embodiments, only a top portion of the outer surface 111 (e.g., having the highest y-coordinate in FIG. 1) that contacts the rear interface 106 may be low friction.

The slide supports 110 are configured to support at least a portion of the slide rail 108. Generally, the slide supports 110 are positioned below (e.g., having a lower y-coordinate) the slide rail 108. The slide supports 110 are adjustable in the y-direction. In some embodiments, one or more of the slide supports 110 may be configured to be manually adjusted. For example, the slide supports 110 may be rotated to extend or to shorten the slide supports 110 via a screw-type mechanism or may be manually positioned using a pin with a series of holes. Additionally or alternatively, one or more of the slide supports 110 may be configured to be pneumatically or electro-mechanically adjusted.

The central stand 116 may be secured relative to the slide rail 108. For example, the central stand 116 may be positioned along the datum 104, which may be located about half-way between the first end 134 and the second end 136. The central stand 116 may be adjustable in the y-direction. For example, the central stand 116 may be adjusted manually, pneumatically, electro-mechanically, or in another suitable way to increase or decrease a distance from an SBT platform 132 or surface (e.g., a floor) on which the SBT 100 is placed.

A central board receiver 140 (hereinafter, "receiver 140") may be attached to the central stand 116. An example of the receiver 140 may be a pocket or cavity that is configured to selectively receive the front interface 120. For example, the front interface 120 may include a structure that is configured to be received in the receiver 140 when the board 102 is positioned on the SBT 100. When the board 102 is removed from the SBT, the front interface 120 may be removed from the board 102 or the front interface 120 may be disengaged from the receiver 140.

The receiver 140 and the front interface 120 enables rotation of the board 102 about the central stand 116. The receiver 140 secures the front interface 120 relative to the central stand 116 such that the front interface 120 can three-dimensionally rotate at least some range about axes parallel to each of the y axis, the x axis, and the z axis.

For example, as shown in FIG. 1, rotation about the axis parallel to the y axis may be limited by the first end 134 and the second end 136 of the slide rail 108. In the depicted embodiment the slide rail 108 is about a semicircle (e.g., about 180 degrees). Accordingly, the rotation about the axis parallel to the y axis may be about 180 degrees. In other embodiments, the slide rail 108 may include a longer arc (e.g., greater than 180 degrees) or a shorter arc (e.g., less than 180 degrees). Accordingly in these and other embodiments, the rotation about the axis parallel to the y axis may be greater than or less than 180 degrees.

Rotation about the axes parallel to the x axis and/or the z axis (e.g., a central axis 142 of FIG. 1, described below) may be limited by the functionality of the SBT 100. For instance, the rotation about the axes parallel to the x axis and/or the z axis may be about fifty degrees to about negative fifty degrees. Such rotation may enable the board 102 to tilt about the central axis 142 as well as enable a rear portion of the board 102 to be elevated (e.g., increased in a y direction) relative to a front portion of the board 102. As the board 102 slides along the slide rail 108, the axes parallel to the x axis and z axis rotate with the board 102.

In some embodiments, the receiver 140 may be configured as a hemispherical surface or a roller bearing. The hemispherical surface or the roller bearing may enable rotation about the central axis 142 of the board 102. Thus, the board 102 may rotate about the central stand 116 and tilt about the central axis 142 of the board 102.

In some embodiments, the front interface 120 may include a hemispherical surface that may be received in the receiver 140. Alternatively, in some embodiments, the front interface 120 may include a pocket and the receiver 140 may include a hemispherical surface or a roller bearing.

The rear interface 106 is configured to mount or to be otherwise coupled to a rear portion of the board 102. The rear interface 106 is configured to contact the slide rail 108 when the board 102 is positioned on the SBT 100 and/or when the SBT 100 is in use. In addition, when a user is moving the board 102 relative to the SBT 100, the rear interface 106 may slide relative to the outer surface 111 of the slide rail 108.

In some embodiments, the rear interface 106 includes rear edge protectors. The rear edge protectors may be positioned over portions of the rear edges of the board 102. The rear edge protectors may prevent or reduce damage to the edges of the board 102, while allowing movement of the board 102 relative to the slide rail 108. The rear edge protectors may be temporarily attached to the board 102. For example, the rear edge protectors may be held in place by one or more elastic bands, adhered (temporarily) to the portions of the board 102, or may be press-fit to the board 102.

In embodiments in which the rear interface 106 includes rear edge protectors, the tilt of the board 102 is primarily controlled by the front interface 120. The board 102 may be twisted by rotating the front portion of the board 102 about the central axis 142 and maintaining the rear interface 106 in contact with the slide rail 108.

Additionally, in some embodiments, the rear interface 106 includes a rear tilt interface. The rear tilt interface includes a round contact element that is configured to contact the outer surface 111 of the slide rail 108. The round contact element elevates the board 102 from the outer surface 111. The round contact element enables the rear portion of the board 102 to tilt similar to the front portion (e.g., rotate about the central axis 142 or a parallel axis). In embodiments in which the rear interface 106 includes the rear tilt interface, the user can rotate the rear portion of the board 102 in a first direction while tilting the front portion of the board 102 in a second direction that is substantially opposite the first direction. Rotation of the rear portion in the first direction with rotation of the front portion in the second direction may twist the snowboard and may simulate the AASI performance concept of twist. In addition, the user can rotate the rear portion in a first direction while tilting the front portion of the snowboard in the same direction. Rotation of the rear portion and the front portion in the first direction tilts the snowboard and may simulate the AASI performance concept of tilt. Some additional details of the front interface 120 and the rear interface 106 are provided elsewhere in this disclosure.

The return assist cord 130 may include a first end 151 and a second end 153. The first end is configured to attach to the rear portion or the end 155 of the board 102. The second end 153 of the return assist cord 130 is configured to be attached a bracket that is substantially aligned with the central position 104 of the SBT 100. For example, the second end 153 may be connected to an overhead bracket (not depicted in FIG. 1). The overhead bracket may be positioned on the ceiling or a frame that is positioned adjacent to the SBT 100, for instance.

The return assist cord 130 may be constructed of an elastic material such as a shock cord or bungee cord. The return assist cord 130 may provide two reactive forces. A first may be in the positive y direction and results from a user standing on the board 102. The force in the positive y direction reduces weight on the rear portion (e.g., near the slide rail 108) of the board 102 that is imposed by the user. The return assist cord 130 may accordingly encourage the user to place more of their weight on the front portion (e.g., near the central stand 116) of the board 102 during use of the SBT 100. Additionally, the return assist cord 130 may simulate a floating feeling of a rear foot of the user.

The second reactive force acts to return the board 102 to the central position 104. For example, the user may rotationally displace the board 102 from the central position 104 towards the first end 134. The return assist cord 130 stretches and acts to return the snowboard to the central position 104. The return assist cord 130 may accordingly simulate a substantially constant motion that may occur on a mountain slope and may assist a user in strengthening muscles associated with this aspect of snowboarding. In addition, the return assist cord 130 may prevent or reduce instance of the board 102 sliding off the ends 134 and 136 of the slide rail 108.

The return assist cord 130 is adjustable in length for the trainee's weight and height and for configuration of the SBT 100. In addition, the return assist cord 130 is adjustable in reactive forces. For example, a return assist cord 130 with less elasticity (e.g., lower reactive forces) may be used for a more experienced user while a return assist cord 130 with more elasticity (e.g., higher reactive forces) may be used with a beginner.

In the depicted embodiment, the SBT 100 includes an adjustment plate 126. The adjustment plate 126 is connected to the central stand 116 and the SBT platform 132. The adjustment plate 126 is configured to move in the z-direction and the negative z-direction. In FIG. 1, the motion of the adjustment plate 126 is shown by arrow 144. The adjustment plate 126 may enable adjustment of the central stand 116 relative to the slide rail 108 to accommodate positioning of snowboards (e.g., 102) having multiple of snowboard lengths using the same slide rail 108. For example, a first snowboard that may have a length of about sixty-five centimeters (cm) may be supported by placement of the central stand 116 at a first distance from the second slide support 110B. A second snowboard that may have a length of about fifty-five cm may be supported by placement of the central stand 116 at a second distance from the second slide support 110B. In this example, the first distance is greater than the second distance.

In the depicted embodiment, the motion of the adjustment plate 126 is in the z-direction. In some embodiments, the motion of the adjustment plate 126 may additionally or alternatively be in the x-direction. For instance, in embodiments in which the slide rail 108 is in an irregular shape, the adjustment plate 126 may move in the x-direction.

Generally, a user of the SBT 100 may be positioned between the central stand 116 and the slide rail 108 when the board 102 is properly positioned on the SBT 100. Without the adjustment plate 126 the central stand 116 may be positioned under a front foot of the user, another slide rail 108 may be utilized, or the slide rail 108 may be positioned under a back foot of the user.

In the depicted embodiment, the SBT 100 includes a balance/focus rope 122. The balance/focus rope 122 may hang from a frame 124 positioned adjacent to or forward of the SBT 100. The balance/focus rope may provide a support for a user of the SBT 100. In addition, the balance/focus rope 122 may be a component on which a user may focus during use. The focus on the balance/focus rope 122 may assist the user to shift their weight forward (e.g., towards a front portion of the snowboard). As the user improves, the use of the balance/focus rope 122 for support may lessen. The balance/focus rope 122 may be used by a beginning user or when an experienced user repositions or reconfigures the SBT 100, for instance. The balance/focus rope 122 may assist users with focusing forward as they practice on the SBT 100, which may assist in positioning them centered on a front portion of the board 102. The balance/focus rope 122 may comprise a flexible or stretchable fabric. The balance/focus rope 122 may also be attached to a ceiling adjacent to or forward of the SBT 100.

In some embodiments, the balance/focus rope 122 may be attached to the same frame as the return assist cord 130. For example, the frame may be positioned behind (e.g., having a larger z dimension) the SBT 100. The frame may extend over the user and include an overhead bracket from which the return assist cord 130 is attached as well as a second bracket from which the balance/focus rope 122 is attached. In some embodiments, the SBT 100 may not include the balance/focus rope 122. Additionally or alternatively, the SBT 100 may include a harness system to support the user during use.

The SBT 100 of FIG. 1 includes the SBT platform 132. The SBT platform 132 provides a base for the slide supports 110, the central stand 116, and the adjustment plate 126. The SBT platform 132 may stabilize the SBT 100. By stabilizing the SBT 100, the potential for injury of a user may be reduced. In the depicted embodiment, the SBT platform 132 is T-shaped in the xz plane (e.g., the top view of FIG. 1). In some embodiments, the SBT platform 132 may include one or more separate bases for one or more of the slide supports 110 and the central stand 116/adjustment plate 126. In these and other embodiments, the SBT platform 132 may be shaped as four circular or rectangular portions, or a larger rectangular portion with one or more smaller portions, etc. In some embodiments, the SBT platform 132 may be secured to a floor or another platform.

Modifications, additions, or omissions may be made to the SBT 100 without departing from the scope of the present disclosure. For example, the SBT 100 may omit the SBT platform 132, or may be installed directly on a floor, the slide rail 108 may be substantially fixed level, the slide supports 110 may be fixed to the SBT platform 132 via adjustment plates similar to the adjustment plate 126, multiple slide rails may be used depending on a length of the board 102, or the board 102 may be a component of the SBT 100 that is permanently or substantially permanently positioned on the SBT 100.

Figure 2A:
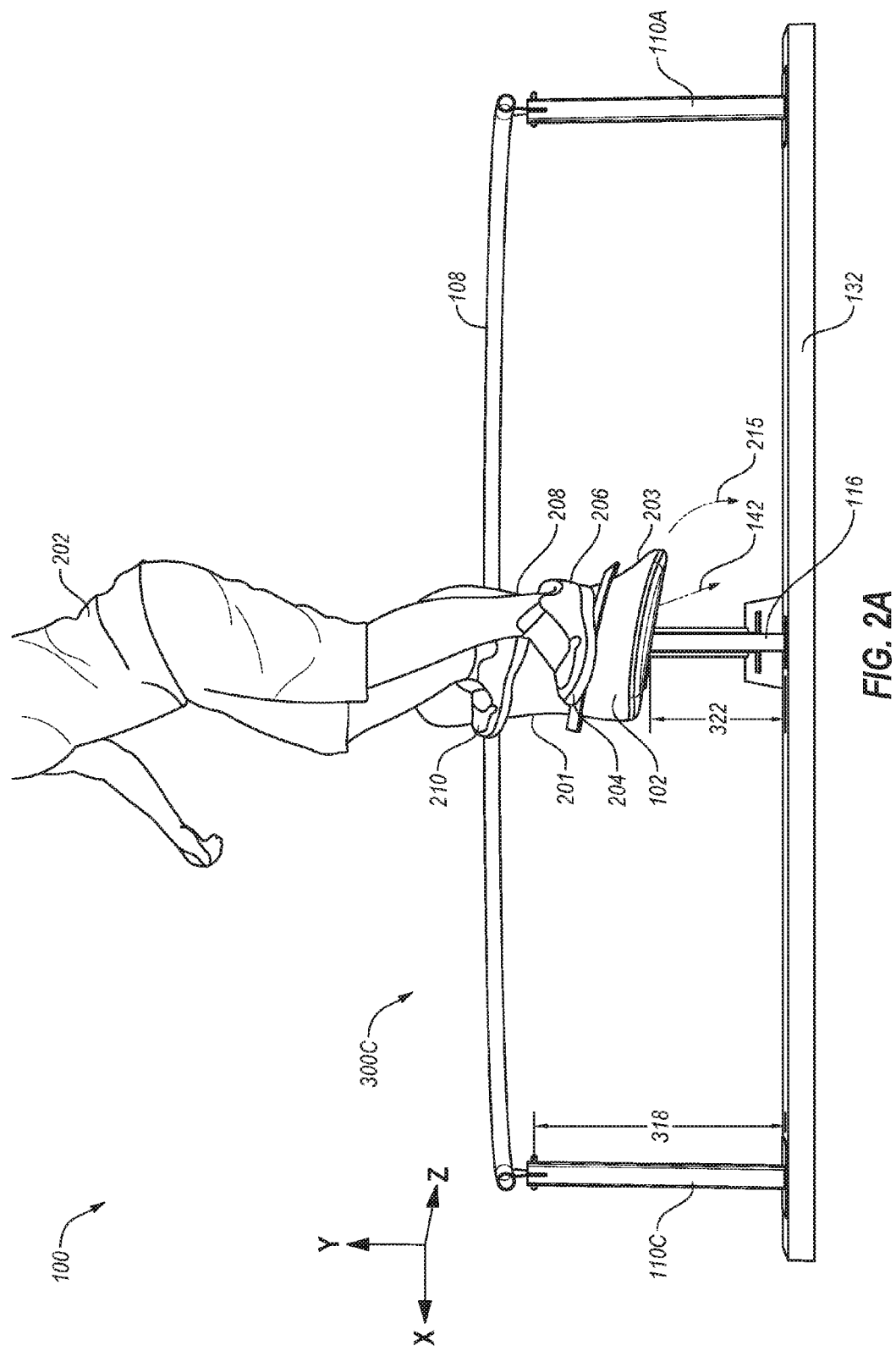
FIG. 2A illustrates another view of the SBT of FIG. 1.
Figure 2B:
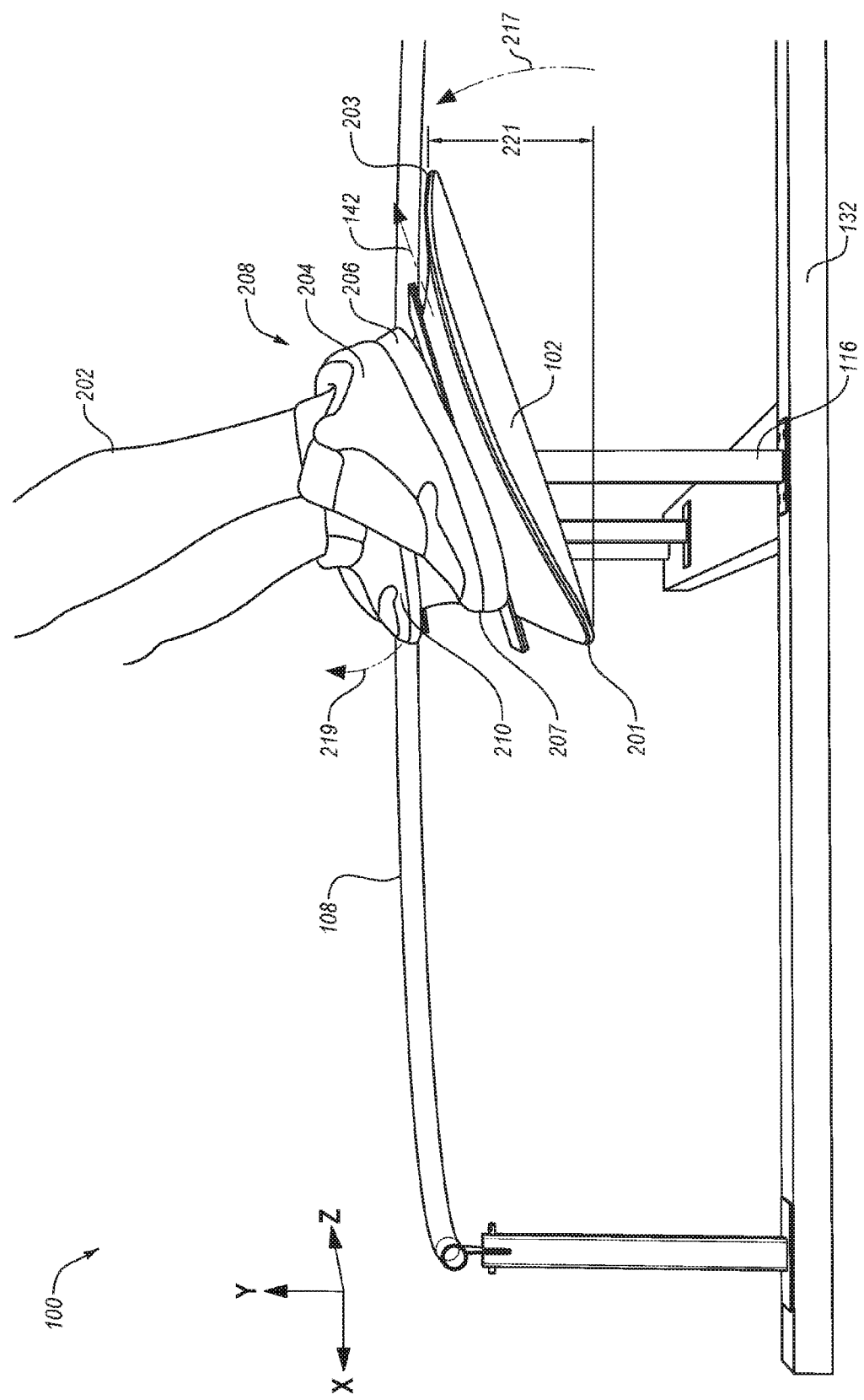
FIG. 2B illustrates another view of the SBT of FIG. 1.

FIGS. 2A and 2B illustrate additional views of the SBT 100 of FIG. 1. FIGS. 2A and 2B illustrate the SBT 100 during activities that result in tilt and twist, respectively. In FIGS. 2A and 2B, a user 202 is situated on the board 102 that is positioned on the SBT 100. The board 102 is in approximately the central position 104. In FIGS. 2A and 2B, multiple components (e.g., 108, 110, 140, 102, and 132) discussed with reference to FIG. 1 are depicted.

With reference to FIGS. 1 and 2A, tilt of the board 102 about the central axis 142 of the board 102 is illustrated. The central axis 142 is substantially parallel to the z-axis of FIG. 2A. In FIG. 2A, the board 102 is depicted rotated or tilted in a clockwise direction relative to the central axis 142, which may simulate the AASI performance concept of tilt.

To tilt the board 102 on the SBT 100, pressure may be applied to a heel 206 of a front foot 204 of the user 202. Additionally, pressure may be applied to a heel 208 of a rear foot 210 of the user 202. A result of the pressure applied to the heels 206 and 208 of the front foot 204 and the rear foot 210 concurrently includes rotation of the board 102 about the central axis 142. The rotation of the board 102 is represented in FIG. 2A by arrow 215.

The rotation 215 in FIG. 2A occurs along the length (e.g., in FIG. 2A the z-dimension) of the board 102 (e.g., end to end). Accordingly, a left edge 201 of the board 102 has a greater y-dimension or height above the SBT platform 132 than a right edge 203 of the board 102 along the length. The tilt occurs because the front interface 120 rotates in the receiver 140 about the central axis 142, which enables rotation of the board 102. Additionally, the rear tilt interface of the rear interface 106 enables the rear portion of the board 102 to rotate relative to the central axis 142 or another axis that is substantially parallel to the central axis 142. In some embodiments, the tilt is limited by contact between one of the edges 201 or 203 and the slide rail 108. Although not explicitly shown, tilt of the board 102 may also occur by the user 202 applying pressure to the toe of the front foot 204 and to the toe of the rear foot 210. Application of the pressure to the toes of the front foot 204 and the rear foot 210 may result in a tilt in a direction opposite to the arrow 215 of FIG. 2A. Additionally, tilt in the direction opposite to the arrow 215 may result in the right edge 203 of the board 102 being higher or having a larger y-dimension than the left edge 201.

With reference to FIGS. 1 and 2B, twist of the board 102 about the central axis 142 of the board 102 is illustrated. Again, the central axis 142 is substantially parallel to the z-axis of FIG. 2B. In FIG. 2B, the board 102 is depicted with a front portion rotated counterclockwise relative to the central axis 142 while a rear portion of the snowboard is rotated clockwise, which may simulate the AASI performance concept of twist.

To twist the board 102 on the SBT 100, pressure may be applied to a toe 207 of the front foot 204 of the user 202. Additionally, pressure may be applied to the heel 208 of the rear foot 210 of the user 202. A result of the pressure applied to the toe 207 of the front foot 204 and to the heel 208 of the rear foot 210 concurrently is rotation of a front portion of the board 102 about the central axis 142 with an opposite rotation of a rear portion of the board 102. The rotations of the board 102 are represented in FIG. 2B by arrows 217 and 219. The first arrow 217 represents the counterclockwise rotation of the front portion of the board 102. The second arrow 219 represents the clockwise rotation of the rear portion of the board 102.

The rotations represented by arrows 217 and 219 in FIG. 2B occur along a portion of the length (e.g., again in FIG. 2B the z-dimension) of the board 102. Accordingly, at a front portion of the board 102, the left edge 201 of the board 102 has a lower y-dimension than the right edge 203 of the board 102. The right edge 203 may be a first distance 221 higher than the left edge 201. At a rear portion of the board 102, the left edge 201 of the board 102 may have a lower y-dimension than the right edge 203 of the board 102, but the difference between the left edge 201 and the right edge 203 may be less than the first distance 221. Alternatively, the left edge 201 may have the same y dimension as the right edge 203 (e.g., equal or substantially equal heights above the SBT platform 132) or may have a greater y dimension than the right edge 203 (e.g., a distance from the left edge 201 to the SBT platform 132 is greater than a distance from the right edge 203 to the SBT platform 132).

The twist occurs because the front interface 120 rotates in the receiver 140 about the central axis 142, which enables rotation of the board 102. Additionally, the rear tilt interface of the rear interface 106 enables the rear portion of the board 102 to rotate relative to the central axis 142 or another axis that is substantially parallel to the central axis 142. In contrast to FIG. 2A, the rotations in FIG. 2B are in opposite or substantially opposite directions. When these rotations are in opposite directions, the board 102 twists along its length.

Although not explicitly shown, twist of the board 102 may also occur by the user 202 applying pressure to the toe of the front foot 204 and to the heel 208 of the rear foot 210. Application of the pressure to the toe of the front foot 204 and to the heel 208 the rear foot 210 may result in a twist in a direction opposite. In particular, the rear portion of the board 102 may rotate in a direction opposite to the arrow 219 of FIG. 2B and the front portion of the board 102 may rotate in a direction opposite to the arrow 217. Additionally, twist in the direction opposite to that shown in FIG. 2B may result in the left edge 201 being higher or having a larger y-dimension than the right edge 203 at the front portion. Additionally, the opposite twist may include less of a difference between the left edge 201 and the right edge 203 at the rear portion of the board 102, the left edge 201 having the same height or y dimension as the right edge 203, or the left edge 201 being lower or having a smaller y-dimension than the right edge 203.

Figure 3A:
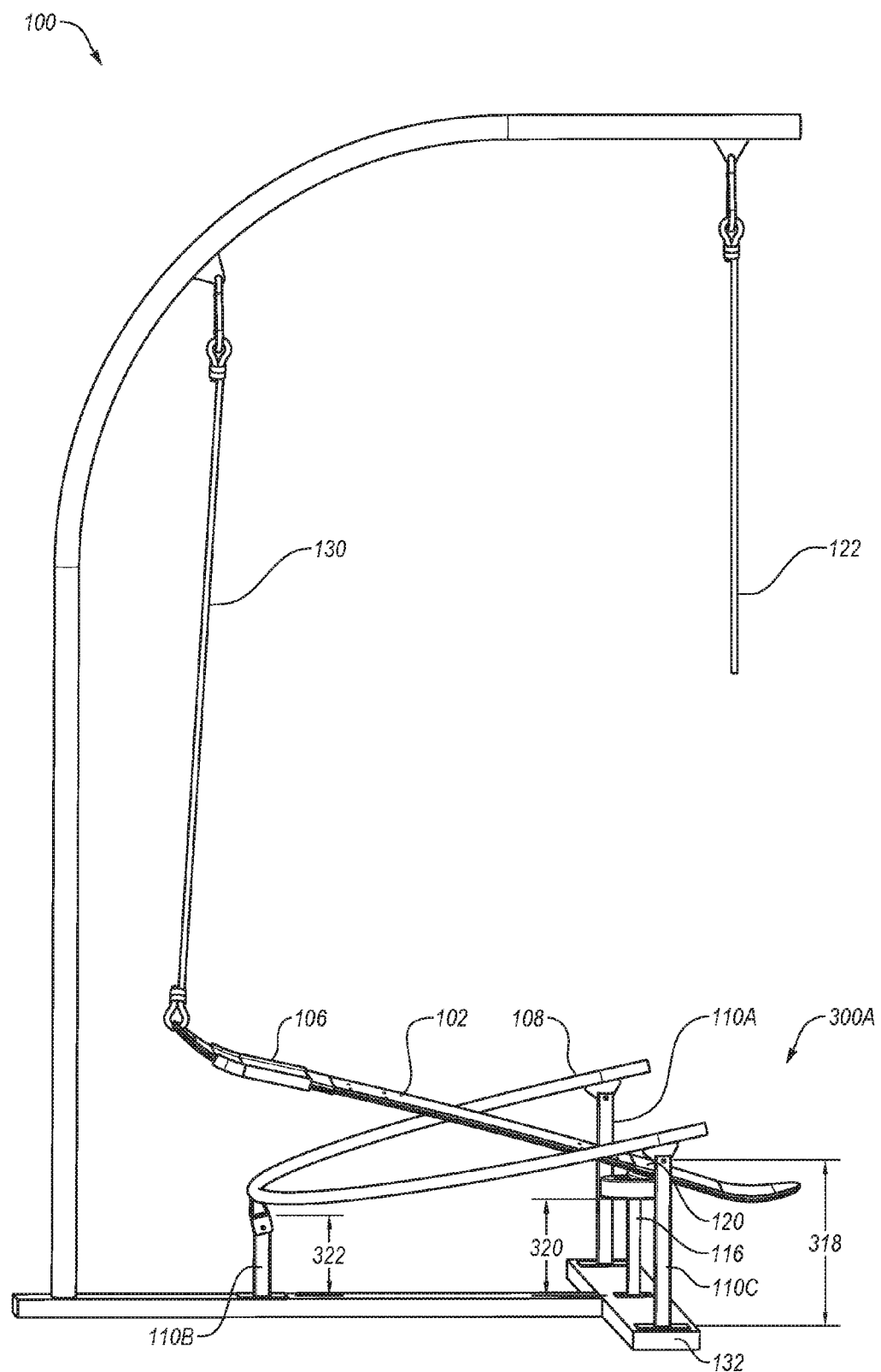
FIG. 3A illustrates another view of the SBT of FIG. 1.
Figure 3B:
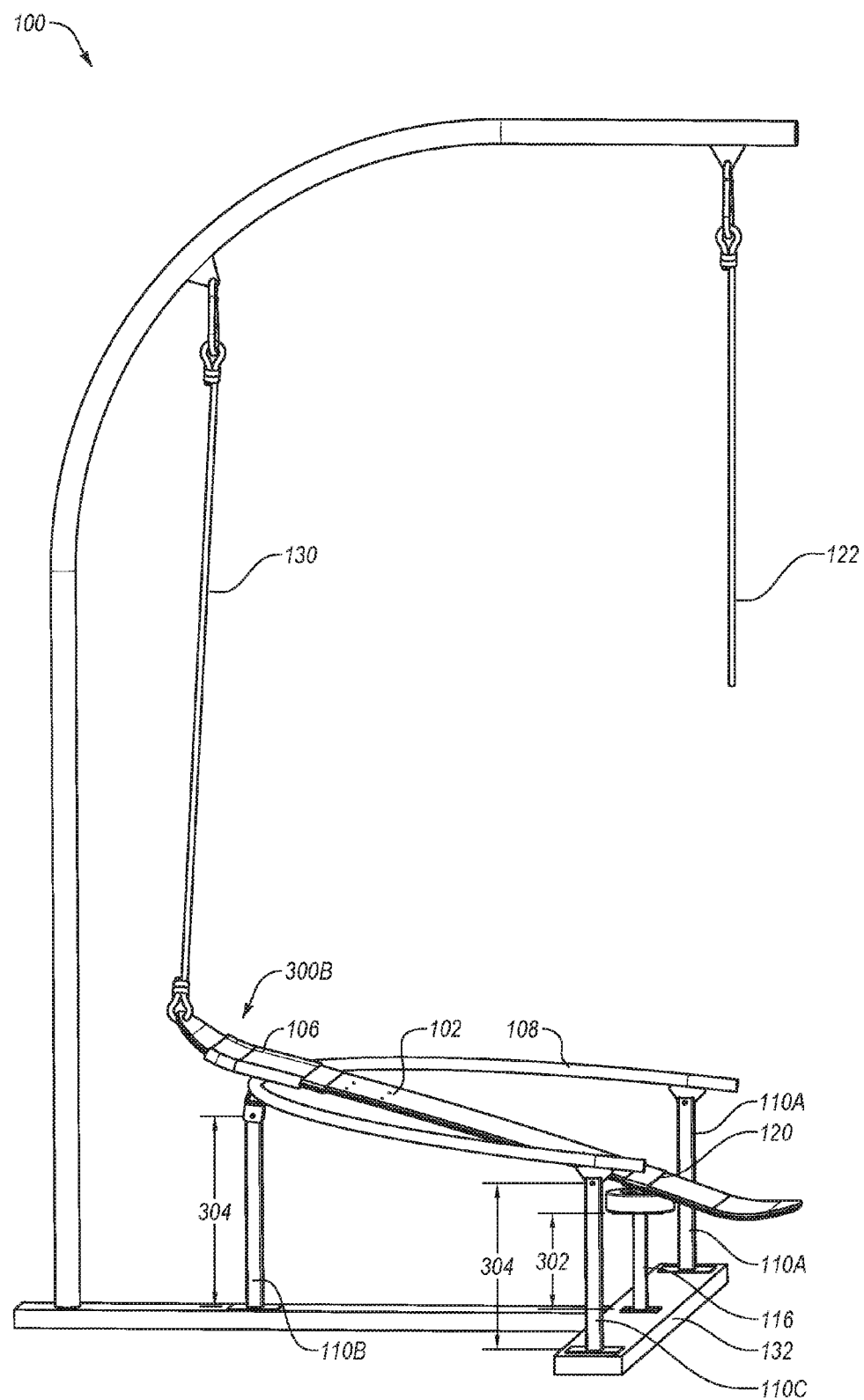
FIG. 3B illustrates another view of the SBT of FIG. 1.

FIGS. 3A, 3B, and 2A illustrate the SBT 100 in a first configuration 300A, a second configuration 300B, and a third configuration 300C. In FIGS. 3A and 3B, multiple components (e.g., 130, 120, 116, 106, 122, 110, 140, and 132) discussed with reference to FIG. 1 are depicted. To position the SBT 100 in each of the configurations 300A-300C one or more of the slide supports 110 and the central stand 116 are adjusted to a particular height relative to one another and/or to the SBT platform 132. In FIGS. 3A, 3B, and 2A, the board 102 is positioned in the SBT 100 may be configured in one or more of the configurations 300A-300C with or without the board 102. Although not explicitly shown in FIGS. 3A and 3B, in each of the configurations 300A-300C, the board 102 may tilt or twist about the central axis 142 as discussed with reference to FIGS. 2A and 2B.

With reference to FIG. 3A, a first configuration 300A is depicted. In the first configuration 300A, the central stand 116 is set at a central stand height 320. The first and the third slide supports 110A and 110C are set at a first support height 318 and the second slide support 110B is set to a second support height 322. The central stand height 320 is less than the first support height 318 and the second support height 322. Additionally, the first support height 318 may be less than the second support height 322. In the first configuration 300A, a front portion of the board 102 may be lower than a rear portion of the board 102. The first configuration 300A may be relatively challenging compared to the other configurations 300A-300C.

With reference to FIG. 3B, a second configuration 300B is depicted. In the second configuration 300B, the central stand 116 is set at a central stand height 302 and each of the slide supports 110 are to a common support height 304. The central stand height 302 is less than the common support height 304. In the second configuration 300B, a front portion of the board 102 may be lower than a rear portion of the board 102. The second configuration 300B may simulate steeper terrain. Additionally, the second configuration 300B may be relatively challenging compared to the other configurations 300A and 300C of FIGS. 3A and 2B. Use of the SBT 100 in the second configuration 300B may involve and thus develop user focus and user balance.

With reference to FIG. 2A, a third configuration 300C is depicted. The third configuration 300C is similar to the second configuration 300B except for the difference between central stand height 302 and the common support height 304 is less than the difference between the central stand height 302 and the common support height 304 in the second configuration 300B. The third configuration 300C may be easier for the user (202) than the second configuration.

The SBT 100 may be configured such that the central stand 116 and each of the slide supports 110 may be set at a common height. When the central stand 116 and each of the slide supports 110 are set at a common height, the board 102 may be level, which may be a relatively easy configuration.

Although three configurations are depicted in FIGS. 3A, 3B, and 2A, embodiments discussed herein may be configured in other ways. For example, the central stand 116 may be set at a second central stand height and each of the slide supports 110 may be set at a third height. The second central stand height may be greater than the third height. Thus, the front portion of the board 102 may be higher than a rear portion of the board 102. This configuration may be relatively easy and may thus be used with a beginning user to assist the user to work on proper edge control, for instance. Additionally, the central stand 116 and the second slide support 110B may be set to a center height. The first and third slide supports 110A and 110C may be set to an outside support height. The outside support height may be greater than the center height. This configuration may simulate steep and uneven terrain, for instance. Moreover, each of the slide supports 110 and/or the central stand 116 may be set at a different height, the slide supports 110 may be set to progressively lower (or higher) heights, a portion of the slide rail 108 may be removed, or motion of the board 102 may be limited to a portion of the slide rail 108. Moreover, in some embodiments, one or more of the slide supports 110 or the central stand 116 may not include an adjustable height. For example, the central stand 116 may stay at a similar height.

FIGS. 4A and 4B depict an embodiment of the front interface 120 and an embodiment of the rear interface 106 mounted on the board 102. FIG. 4A depicts a bottom surface 404 of the board 102 and FIG. 4B depicts a top surface 402 of the board 102.

With reference to FIG. 4A, the front interface 120 may include a bracket 401. The bracket 401 may secure the front interface 120 relative to the board 102. The bracket 401 may include a rectangular portion 405 and a disk 403. The rectangular portion 405 extends laterally (edge-to-edge) across the board 102 and may be attached with fasteners at a first end 407 and a second end 409. The disk 403 may be positioned in a center portion of the bracket 401. The disk 403 may prevent or reduce damage to the board 102 through contact between the bracket 401 and a receiver (e.g., the receiver 140).

The front interface 120 of FIGS. 4A and 4B includes a roller bearing 411. The roller bearing 411 may extend from the disk 403 and may be centered in the disk 403. The roller bearing 411 is sized and configured to be secured to the receiver. The roller bearing 411 may include a bearing 413 that enables three-dimensional rotation.

With reference to FIG. 4B, the rectangular portion 405 of the bracket 401 extends across the top surface 402 of the board 102. The rectangular portion 405 includes fasteners 415 that are arranged to interface with front binding fasteners of the board 102.

Referring back to FIG. 4A, the rear interface 106 may include a rear tilt interface 600. The rear tilt interface 600 includes a rear rectangular portion 431 and a round contact element 602. The rear rectangular portion 431 extends laterally (edge-to-edge) across the board 102. The rear rectangular portion 431 is attached with fasteners at a first end 412 and a second end 414.

The round contact element 602 extends from the rear rectangular portion 431. The round contact element 602 may be centered between the edges of the board 102. The round contact element 602 is configured to contact the low friction surface of the slide rail (e.g., the outer surface 111 of the slide rail 108). The round contact element 602 includes a central tube 601 that is welded or otherwise attached to the rear rectangular portion 431. An outer tube 603 is positioned on a portion of the central tube 601. The outer tube 603 may be constructed of a plastic in some embodiments.

The rear interface 106 includes rear edge protectors 419A and 419B. The rear edge protectors 419A and 419B may be positioned over portions of the rear edges 421A and 421B of the board 102. For example, in FIGS. 4A and 4B, a first rear edge protector 419A may be placed on a first edge 421A and a second rear edge protector 419B may be placed on a second edge 421B.

The rear edge protectors 419A and 419B may prevent or reduce damage to the edges 421A and 421B of the board 102, while allowing movement of the board 102 relative to a slide rail (e.g., the slide rail 108). For example, without the rear edge protectors 419A and 419B, use of the board 102 with the SBT 100 may damage or wear the edges 421A and 421B. The rear edge protectors 419A and 419B can reduce the damage by reducing friction between the edges 421A and 421B and the slide rail. For instance, the slide rail contacts the rear edge protectors 419A and 419B instead of the edges 421A and 421B directly.

The rear edge protectors 419A and 419B may be temporarily attached to the board 102. For example, the rear edge protectors 419A and 419B may be held in place by one or more elastic bands 423. Additionally or alternatively, the rear edge protectors 419A and 419B may be adhered (temporarily) to the portions of the edges 421A and 421B of the board 102, or may be press-fit onto the edges 421A and 421B of the board 102.

A position of the rear edge protectors 419A and 419B may be adjusted. For example, with reference to FIGS. 4A and 1, a distance between the rear edge protectors 419A and 419B and the central stand 116 may be adjusted such that the rear edge protectors 419A and 419B are substantially centered on the slide rail 108 when the front interface 120 is secured in the receiver 140.

With reference to FIG. 4B, the rear rectangular portion 431 of the rear interface 106 extends across the top surface 402 of the board 102. The rear rectangular portion 431 includes fasteners 425 that are arranged to interface with the rear binding fasteners of the board 102. The rear rectangular portion 431 may be attached with fasteners at the first end 412 and the second end 414.

Figure 5:
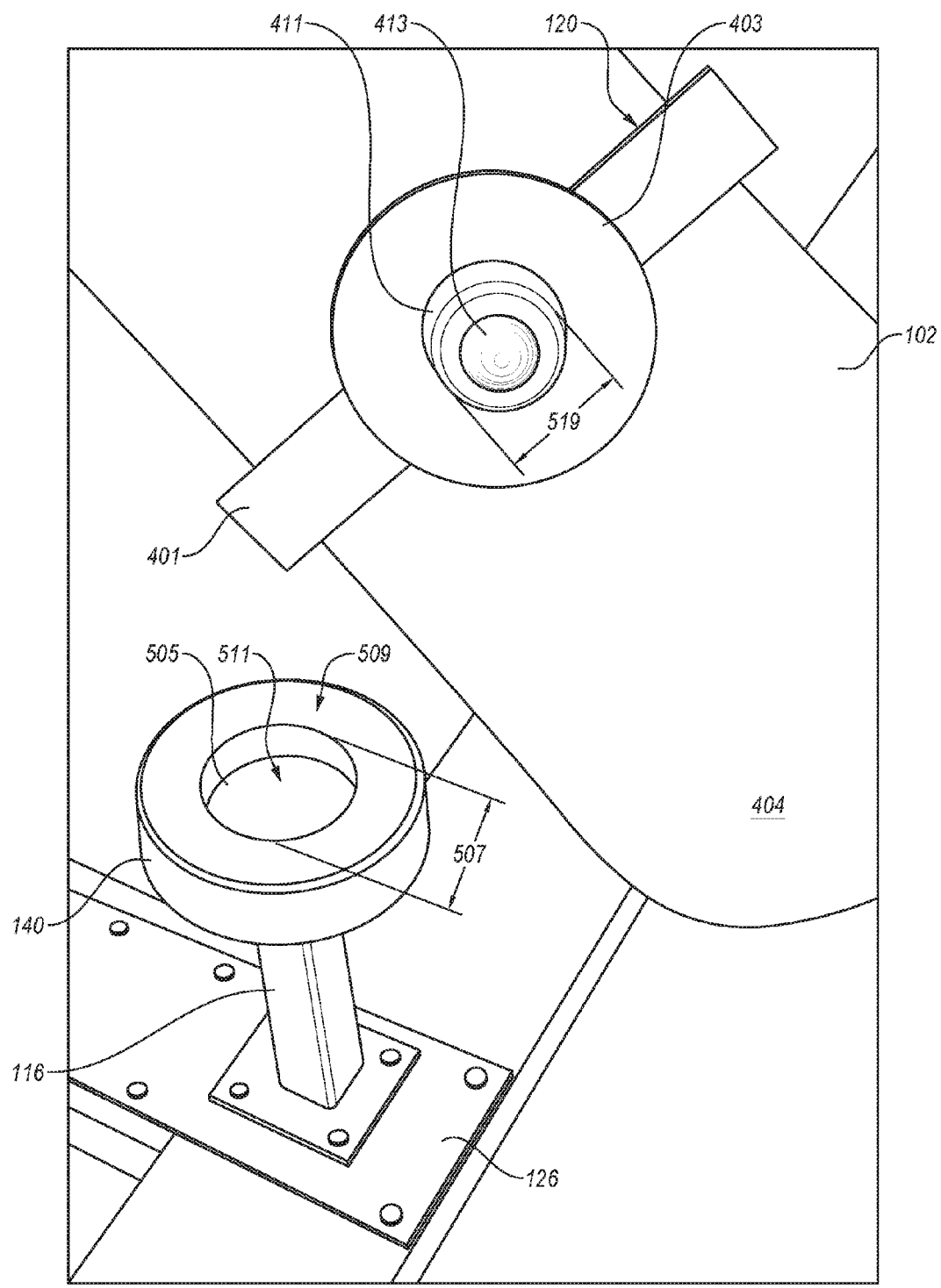
FIG. 5 illustrates another view of the front interface of FIG. 4A.

FIG. 5 depicts the front interface 120 disengaged from the receiver 140. As discussed above, the receiver 140 may be coupled to the central stand 116. The receiver 140 is substantially circular and includes a receiver top surface 509. The receiver top surface 509 may contact and may wear against a portion (e.g., the disk 403) of the bracket 401 around the roller bearing 411. The receiver top surface 509 may be constructed of a rubber or plastic material.

The receiver 140 defines a pocket 505. The pocket 505 is sized to receive the roller bearing 411. For instance, a diameter 507 of the pocket 505 may correspond to a diameter 519 of the roller bearing 411. Accordingly, the roller bearing 411 may be received in the receiver 140 and secured relative to the central stand 116 to enable some three dimensional rotation. Additionally, an outer surface of the bearing 413 may be configured to contact an inner surface 511 of the pocket 505.

In the depicted embodiment, the front interface 120 includes the roller bearing 411 and the central stand 116 is coupled to the receiver 140. In other embodiments, the front interface 120 may include the receiver 140 or a similar structure and the central stand 116 may be coupled to the roller bearing 411.

Figure 6:
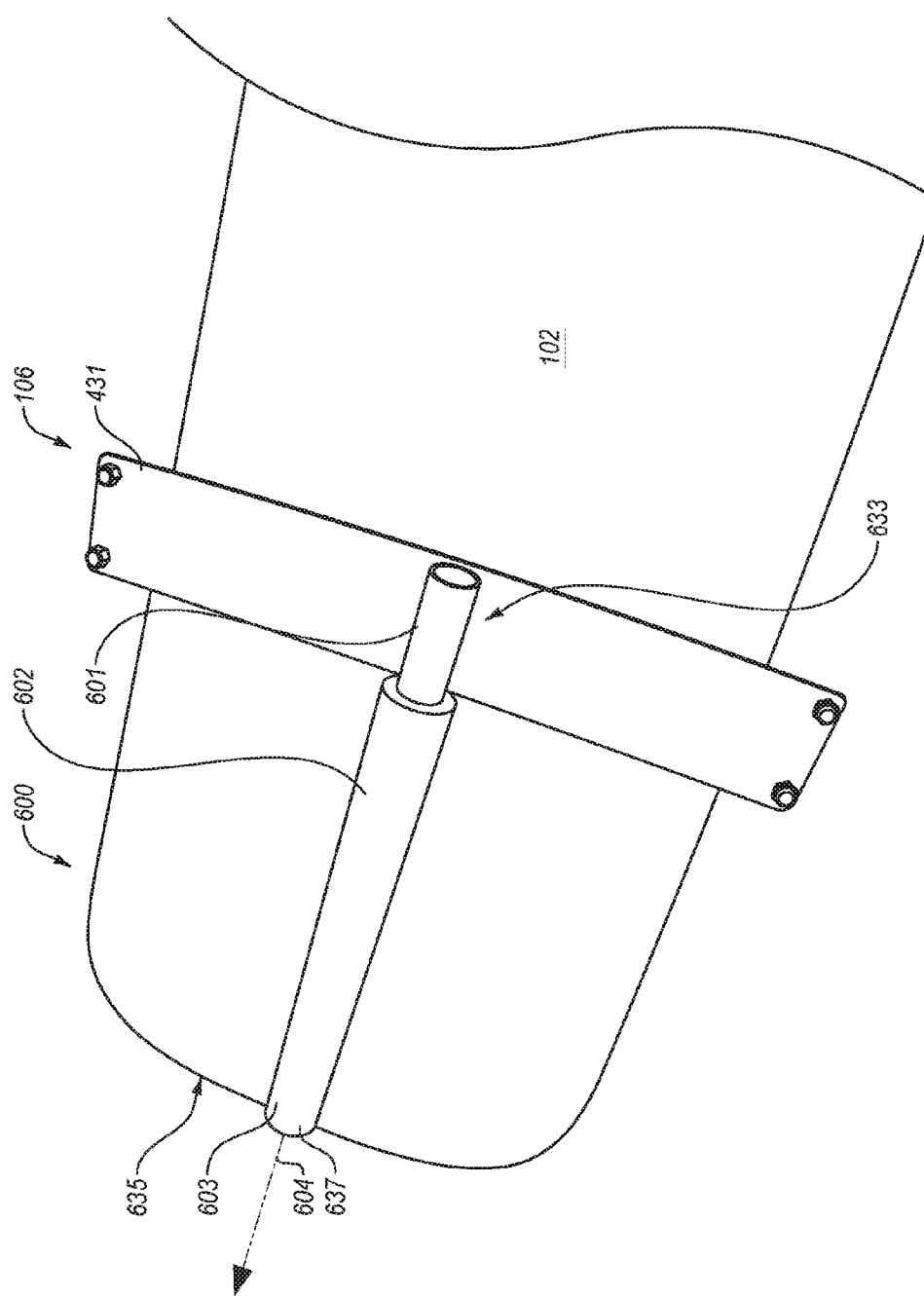
FIG. 6 illustrates another view of the rear interface of FIG. 4A.

FIG. 6 illustrates an example embodiment of the rear interface 106 mounted to a board 102. The rear interface 106 is configured to mount or to be otherwise coupled to a rear portion of the board 102. In the depicted embodiment, the rear interface 106 includes the rear tilt interface 600 introduced in FIG. 4B.

The rear tilt interface 600 includes the rear rectangular portion 431 connected to the round contact element 602. The round contact element 602 includes the central tube 601. A first end of the central tube 601 is connected to the rear rectangular portion 431 at a first end 633. The central tube 601 is connected to an end 635 of the board 102 at a second end 637.

The outer tube 603 is positioned on the central tube 601. In the depicted embodiment, the outer tube 603 is a pipe or tube that is placed on the central tube 601. In other embodiments, the outer tube 603 may include a rounded surface instead of a pipe or cylinder. For example, the outer tube 603 may include an arc that covers the central tube 601. Alternatively, the outer tube 603 may be omitted.

With reference to FIGS. 1 and 6, the outer tube 603 of the round contact element 602 is configured to contact the outer surface 111 of the slide rail 108 of FIG. 1 when the board 102 is positioned on the SBT 100. The round contact element 602 elevates the board 102 from the outer surface 111 of the slide rail 108. For example, during use, the round contact element 602 may contact the outer surface 111 which elevates the rear portion of the board 102 from the slide rail 108. The round contact element 602 enables the board 102 to rotate about a round element axis 604 of the round contact element 602. The round element axis 604 is a central axis of the round contact element 602. In response, at least the rear portion of the board 102 may tilt or rotate relative to the axis 604. Furthermore, the user can rotate the rear portion of the board 102 about the round element axis 604 of the round contact element 602. As described above, rotation of the rear portion of the board 102 about the round element axis 604 may result in twist and/or tilt of the board 102.

In addition, the round contact element 602 and in particular the outer tube 603 enables the rear portion to slide along the slide rail 108. The outer tube 603 may include a low friction surface that contacts the outer surface 111.

FIG. 7 illustrates a block diagram of an example SBT system 700. In the SBT system 700, an example embodiment of the SBT 100 is implemented with a computing system 706. The computing system 706 may communicate with the SBT 100 and/or a user of the SBT 100 to provide an interactive experience. For example, the computing system 706 may provide gaming experience that may be integrated with an animated video feeding into a remote logic controller and that adjusts the SBT 100 through one or more of the configurations 300A-300C, while the gamer attempts to follow an image on the display. Additionally, the SBT 100 can also be used in the home entertainment industry, e.g., the WII® game, which gives feedback on various sporting devices through sensors (e.g., sensors 751) mounted on a user's body or on the SBT 100.

In some embodiments, the SBT 100 may include a data accumulation/communication device 711. The data accumulation/communication device 711 may receive data from one or more sensors 751 configured to measure data indicative of positions of the slide supports 110, the central stand 116, a user (not shown), the board 102, or some combination thereof.

Additionally or alternatively, the data accumulation/communication device 711 may communicate signals to actuators 753 that may re-position one or more of the slide supports 110, the central stand 116, and the board 102. In some embodiments, the data accumulation/communication device 711 may receive signals from the computing system 706 and communicate actuation signals to the actuators 753.

In some embodiments, communication between the computing system 706 and one or more components of the SBT 100 may be via a network 755. For instance, one or more of the sensors 751 may communicate a signal to the computing system 706 via the network 755.

The network 755 may include a wired network, a wireless network, or any combination thereof. The network 755 may include any suitable configuration or configurations including a star configuration, token ring configuration, or other configurations. The network 755 may include a local area network (LAN), a wide area network (WAN) (e.g., the Internet), and/or other interconnected data paths across which multiple devices may communicate. The network 755 may also be coupled to or include portions of a telecommunications network that may enable communication of data in multiple communication protocols. In some embodiments, the network 755 includes BLUETOOTH® communication networks and/or cellular communication networks for sending and receiving data including via short messaging service (SMS), multimedia messaging service (MMS), hypertext transfer protocol (HTTP), direct data connection, wireless application protocol (WAP), e-mail, and the like.

The computing system 706 may include a training module 710 and/or a game module 712. The training module 710 and/or the game module 712 may be configured to be implemented with the SBT 100 to provide an interactive experience with the user of the SBT 100. For example, the training module 710 may have pre-loaded programs to develop certain skills of a user. Additionally, the game module 712 may include games that receive input data from the sensors 751 and/or communicate command signals to the data accumulation/communication device 711.

The training module 710 and/or the game module 712 may be implemented using hardware including a processor, a microprocessor (e.g., to perform or control performance of one or more operations), a field-programmable gate array (FPGA), or an application-specific integrated circuit (ASIC). In some other instances, the training module 710 and/or the game module 712 may be implemented using a combination of hardware and software. Implementation in software may include rapid activation and deactivation of one or more transistors or transistor elements such as may be included in the hardware of a computing system. Additionally, software defined instructions may operate on information within transistor elements. Implementation of software instructions may at least temporarily reconfigure electronic pathways and transform computing hardware.

The computing system 706 may be configured for snowboard training or gaming via implementation with the SBT 100. The computing system 706 may include one or more processors 704, memory 708, a communication unit 702, a user input device 714 that may include or be communicatively coupled to the SBT 100, and a data storage 701 that includes the training module 710 and/or the game module 712 (modules 710/712).

The processor 704 may include any suitable special-purpose or general-purpose computer, computing entity, or processing device including various computer hardware or software modules and may be configured to execute instructions stored on any applicable computer-readable storage media. For example, the processor 704 may include a microcontroller, a microprocessor, a digital signal processor (DSP), an ASIC, an FPGA, or any other digital or analog circuitry configured to interpret and/or to execute program instructions and/or to process data. Although illustrated as a single processor in FIG. 7, the processor 704 may more generally include any number of processors configured to perform individually or collectively any number of operations described in the present disclosure. Additionally, one or more of the processors 704 may be present on one or more different electronic devices or computing systems. In some embodiments, the processor 704 may interpret and/or execute program instructions and/or process data stored in the memory 708, the data storage 701, or the memory 708 and the data storage 701. The processor 704 may fetch program instructions from the data storage 701 and load the program instructions in the memory 708. After the program instructions are loaded into the memory 708, the processor 704 may execute the program instructions.

The memory 708 and data storage 701 may include computer-readable storage media for carrying or having computer-executable instructions or data structures stored thereon. Such computer-readable storage media may include any available media that may be accessed by a general-purpose or special-purpose computer, such as the processor 704. By way of example, and not limitation, such computer-readable storage media may include tangible or non-transitory computer-readable storage media including RAM, ROM, EEPROM, CD-ROM or other optical disk storage, magnetic disk storage or other magnetic storage devices, flash memory devices (e.g., solid state memory devices), or any other storage medium which may be used to carry or store desired program code in the form of computer-executable instructions or data structures and that may be accessed by a general-purpose or special-purpose computer. Combinations of the above may also be included within the scope of computer-readable storage media. Computer-executable instructions may include, for example, instructions and data configured to cause the processor 704 to perform a certain operation or group of operations.

The communication unit 702 may include one or more pieces of hardware configured to receive and send communications. In some embodiments, the communication unit 702 may include one or more of an antenna, a wired port, and modulation/demodulation hardware, among other communication hardware devices. For instance, the communication unit 702 may be configured to receive a communication from outside the computing system 706 and present the communication to the processor 704 or to send a communication from the processor 704 to another device or network.

The user input device 714 may include one or more pieces of hardware configured to receive input from and/or provide output to a user. In some embodiments, the user input device 714 may be coupled to or include the SBT 100. In some embodiments, the user input device 714 may include one or more of the sensors 751, the actuators 753, a speaker, a microphone, a display, a keyboard, a touch screen, and a holographic projection, among other hardware devices. In these and other embodiments, the user input device 714 may be configured to receive input from a user of the computing system 706.

The modules 710/712 may include program instructions stored in the data storage 701. The processor 704 may be configured to load the modules 710/712 into the memory 708 and execute the modules 710/712. Alternatively, the processor 704 may execute the modules 710/712 line-by-line from the data storage 701 without loading them into the memory 708. When executing the modules 710/712, the processor 704 may be configured for equality verification using relational encryption as described elsewhere herein.

Modifications, additions, or omissions may be made to the computing system 706 without departing from the scope of the present disclosure. For example, in some embodiments, the computing system 706 may not include the user input device 714. In some embodiments, the different components of the computing system 706 may be physically separate and may be communicatively coupled via any suitable mechanism. For example, the data storage 701 may be part of a storage device that is separate from a server, which includes the processor 704, the memory 708, and the communication unit 702, that is communicatively coupled to the storage device.

Thus, an aspect of the present disclosure may be a snowboard trainer (SBT). The SBT may include an SBT platform, a slide rail, slide supports, a central stand, and a front interface. The slide rail may extend from a first end to a second end. The slide supports may connect the slide rail to the SBT platform. The slide supports may be configured to support the slide rail relative to the SBT platform. The central stand may be positioned relative to the slide rail on the SBT platform and positioned between the first end and the second end of the slide rail. The central board receiver may be connected to the central stand. The front interface may be configured to be secured to a front portion of a snowboard. The front interface may include a roller bearing sized to be retained in the central board receiver such that when the roller bearing may be received in the central board receiver, the front interface three-dimensionally rotates relative to the central stand. The SBT may include a rear interface that may be configured to be secured to a rear portion of the snowboard. The SBT may include a return assist cord that may include a first end and a second end and may be comprised of an elastic material. The first end may be configured to be attached to a rear portion of the snowboard. The second end may be attached to a bracket that may be substantially aligned with a central position of the SBT. The return assist cord may be configured to reduce weight on the rear portion of the snowboard that may be imposed by the user and to help return the snowboard to the central position following rotational displacement of the snowboard from the central position. In detail, the heights of one or more or a combination of the slide supports and the central stand may be adjustable relative to the SBT platform. The central stand may be positioned relative to the slide rail such that when the front interface is secured to the snowboard and the roller bearing is retained in the central board receiver, the rear interface secured to the snowboard contacts an outer surface of the slide rail. The rotation of the front interface relative to the central stand may include a rotational displacement of the rear portion of the snowboard relative to the slide rail while the rear interface maintains contact with the outer surface of the slide rail and a tilt of the snowboard relative to a central axis of the snowboard. The rear interface may include a rear tilt interface that may include a round contact element. The round contact element may contact the outer surface of the slide rail to elevate the rear portion of the snowboard from the slide rail and may enable rotation of at least the rear portion of the snowboard about to a round element axis. The rear interface may further include rear edge protectors that are positioned over portions of rear edges of the snowboard, the rear edge protectors being configured to reduce damage to the rear edges of the snowboard while allowing movement of the snowboard relative to the slide rail.

Another aspect of the present disclosure is an SBT that may include a slide rail, a central stand, a central board receiver, a rear interface, and a front interface. The slide rail may extend from a first end to a second end. The central stand may be positioned between the first end and the second end of the slide rail. The central board receiver may be connected to the central stand. The rear interface may be configured to be secured to a rear portion of a snowboard. The front interface may be configured to be secured to a front portion of the snowboard. The front interface including a roller bearing may be size to be retained in the central board receiver such that when the roller bearing is received in the central board receiver, the front interface three-dimensionally rotates relative to the central stand. The SBT may include three slide supports that support the slide rail. The heights of one or more or a combination of the slide supports and the central stand may be adjustable such that the SBT may be capable of being arranged in multiple configurations. The SBT may include an SBT platform and an adjustment plate that may be connected to the SBT platform and the central stand. The adjustment plate may be configured to enable movement of the central stand relative to the slide rail to accommodate positioning of snowboards having multiple snowboard lengths. The SBT may include a return assist cord that may include a first end and a second end and may be comprised of an elastic material. The first end may be configured to be attached to a rear portion of the snowboard. The second end may be attached to a bracket that may be substantially aligned with a central position of the SBT. The return assist cord may be configured to reduce weight on the rear portion of the snowboard that may be imposed by the user and to help return the snowboard to the central position following rotational displacement of the snowboard from the central position. In detail, the central stand may be positioned relative to the slide rail such that when the front interface is secured to the snowboard and the roller bearing is retained in the central board receiver, the rear interface secured to the snowboard contacts an outer surface of the slide rail. The slide rail may be substantially C-shaped between the first end and the second end and may include a circular cross section. The rear interface may include a rear tilt interface that may include a round contact element that contacts the outer surface of the slide rail to elevate the rear portion of the snowboard from the slide rail and enables rotation of at least the rear portion of the snowboard about a round element axis of the round contact element and rear edge protectors that are positioned over portions of rear edges of the snowboard. The rear edge protectors may be configured to reduce damage to the rear edges of the snowboard while allowing movement of the snowboard relative to the slide rail. The rotation of the front interface relative to the central stand may include a rotational displacement of the rear portion of the snowboard along to the slide rail while the round contact element maintains contact with the outer surface of the slide rail and a tilt of the snowboard relative to a central axis of the snowboard and relative to the round element axis. Additionally or alternatively, the rotation of the front interface relative to the central stand may include a rotational displacement of the rear portion of the snowboard along to the slide rail while the round contact element maintains contact with the outer surface of the slide rail and a twist of the snowboard that may include a first rotation of the front portion of the snowboard in a first direction relative to the central axis and a second rotation of the rear portion of the snowboard in a second direction that may be opposite the first direction relative to the round element axis. The rotation of the front interface relative to the central stand may include a rotational displacement of the rear portion of the snowboard along to the slide rail of about 180 degrees and a tilt of the snowboard relative to a central axis in a range of about fifty degrees to about negative fifty degrees. The rear tilt interface may further include a rear rectangular portion. The round contact element may include a central tube that may be connected to the rear rectangular portion at a first end and configured to be connected to the snowboard at a second end and the round contact element may include an outer tube positioned over a portion of the central tube.

Yet another aspect is an SBT that may include an SBT platform, a slide rail, a central stand, a central board receiver, three slide supports, a rear interface, a front interface, and a return assist cord. The slide rail may extend from a first end to a second end. The three slide supports may support the slide rail relative to the SBT platform. The heights of the slide supports may be adjustable. The central stand may be between the first end and the second end of the slide rail on the SBT platform. The central board receiver may be connected to the central stand. The rear interface may be configured to be secured to a rear portion of a snowboard. The front interface may be configured to be secured to a front portion of the snowboard. The front interface may include a roller bearing that may be size to be retained in the central board receiver such that when the roller bearing may be received in the central board receiver, the front interface three-dimensionally rotates relative to the central stand. The return assist cord may include a first end and a second end and may be comprised of an elastic material. The first end may be configured to be attached to a rear portion of the snowboard. The second end may be attached to a bracket that may be substantially aligned with a central position of the SBT. The return assist cord may be configured to reduce weight on the rear portion of the snowboard imposed by the user and to help return the snowboard to the central position following rotational displacement of the snowboard from the central position. In detail, the central stand may be positioned relative to the slide rail such that when the front interface may be secured to the snowboard and the roller bearing may be retained in the central board receiver, the rear interface secured to the snowboard contacts an outer surface of the slide rail. In detail, the rear interface may include a rear tilt interface that may include a round contact element that contacts the outer surface of the slide rail to elevate the rear portion of the snowboard from the slide rail and enables rotation of at least the rear portion of the snowboard about a round element axis of the round contact element. The rear interface may include rear edge protectors that are positioned over portions of rear edges of the snowboard. The rear edge protectors may be configured to reduce damage to the rear edges of the snowboard while allowing movement of the snowboard relative to the slide rail.

Still another aspect is an SBT system. The SBT system may include an SBT, a computing system implementing a training module and/or a game module and one or more sensors that are configured to measure data indicative of a position of the snowboard relative to the front interface and the slide rail and to communicate the data to the computing system for use in the training module and/or a game module. In detail, the computing system may include one or more processors and the training module and/or the game module may include a non-transitory computer-readable medium having encoded therein programming code executable by the one or more processors to perform training or gaming operations based at least partially on the data.

The embodiments described herein may include the use of a special purpose or general-purpose computer including various computer hardware or software modules, as discussed elsewhere in this disclosure. As used herein, the terms "module" or "component" may refer to specific hardware implementations configured to perform the operations of the module or component and/or software objects or software routines that may be stored on and/or executed by general purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general purpose hardware), specific hardware implementations or a combination of software and specific hardware implementations are also possible and contemplated. In this description, a "computing entity" may be any computing system as previously defined herein, or any module or combination of modulates running on a computing system.

All examples and conditional language recited in the present disclosure are intended for pedagogical objects to aid the reader in understanding embodiments of the invention and the concepts contributed by the inventor to furthering the art, and are to be construed as being without limitation to such specifically recited examples and conditions. Although embodiments of the present inventions have been described in detail, it should be understood that various changes, substitutions, and alterations could be made hereto without departing from the scope of the present disclosure.

What is claimed is:

1. A snowboard trainer (SBT), comprising:
   an SBT platform;
   a slide rail that extends from a first end to a second end;
   one or more slide supports that connect the slide rail to the SBT platform, the slide supports being configured to support the slide rail relative to the SBT platform;
   a central stand positioned relative to the slide rail on the SBT platform, the central stand being positioned between the first end and the second end of the slide rail;
   a central board receiver that is connected to the central stand; and
   a front interface that is configured to be secured to a front portion of a snowboard, the front interface including a roller bearing sized to be retained in the central board receiver such that when the roller bearing is received in the central board receiver, the front interface three-dimensionally rotates about to the central stand,
   wherein heights of one or more or a combination of the slide supports and the central stand are adjustable relative to the SBT platform.

2. The SBT of claim 1, further comprising a rear interface that is configured to be secured to a rear portion of the snowboard.

3. The SBT of claim 2, wherein the central stand is positioned relative to the slide rail such that when the front interface is secured to the snowboard and the roller bearing is retained in the central board receiver, the rear interface secured to the snowboard contacts an outer surface of the slide rail.

4. The SBT of claim 3, wherein rotation relative to the central stand of the front interface includes:
   a rotational displacement of the rear portion of the snowboard relative to the slide rail while the rear interface maintains contact with the outer surface of the slide rail; and a tilt of the snowboard relative to a central axis of the snowboard.

5. The SBT of claim 3, wherein:
the rear interface includes a rear tilt interface that includes a round contact element; and
the round contact element contacts the outer surface of the slide rail to elevate the rear portion of the snowboard from the slide rail and enables rotation of at least the rear portion of the snowboard about to a round element axis.

6. The SBT of claim 5, wherein the rear interface further includes rear edge protectors that are positioned over portions of rear edges of the snowboard, the rear edge protectors being configured to reduce damage to the rear edges of the snowboard while allowing movement of the snowboard relative to the slide rail.

7. The SBT of claim 1, further comprising a return assist cord that includes a first end and a second end and is comprised of an elastic material, wherein:
the first end is configured to be attached to a rear portion of the snowboard;
the second end is attached to a bracket that is substantially aligned with a central position of the SBT; and
the return assist cord is configured to reduce weight on the rear portion of the snowboard that is imposed by a user and to help return the snowboard to the central position following rotational displacement of the snowboard from the central position.

8. A snowboard trainer (SBT), comprising:
a slide rail that extends from a first end to a second end;
a central stand positioned between the first end and the second end of the slide rail;
a central board receiver that is connected to the central stand;
a rear interface that is configured to be secured to a rear portion of a snowboard;
three slide supports that support the slide rail, wherein heights of one or more or a combination of the slide supports and the central stand are adjustable such that the SBT is capable of being arranged in multiple configurations;
a front interface that is configured to be secured to a front portion of the snowboard, the front interface including a roller bearing that is size to be retained in the central board receiver such that when the roller bearing is received in the central board receiver, the front interface three-dimensionally rotates relative to the central stand,
wherein the central stand is positioned relative to the slide rail such that when the front interface is secured to the snowboard and the roller bearing is retained in the central board receiver, the rear interface secured to the snowboard contacts an outer surface of the slide rail.

9. The SBT of claim 8, wherein the slide rail is substantially C-shaped between the first end and the second end and includes a circular cross section.

10. The SBT of claim 8, wherein the rear interface includes:
a rear tilt interface that includes a round contact element that contacts the outer surface of the slide rail to elevate the rear portion of the snowboard from the slide rail and enables rotation of at least the rear portion of the snowboard about a round element axis of the round contact element; and
rear edge protectors that are positioned over portions of rear edges of the snowboard, the rear edge protectors being configured to reduce damage to the rear edges of the snowboard while allowing movement of the snowboard relative to the slide rail.

11. The SBT of claim 10, wherein the rotation of the front interface relative to the central stand includes:
a rotational displacement of the rear portion of the snowboard along to the slide rail while the round contact element maintains contact with the outer surface of the slide rail and a tilt of the snowboard relative to a central axis of the snowboard and relative to the round element axis; or
a rotational displacement of the rear portion of the snowboard along to the slide rail while the round contact element maintains contact with the outer surface of the slide rail and a twist of the snowboard that includes a first rotation of the front portion of the snowboard in a first direction relative to the central axis and a second rotation of the rear portion of the snowboard in a second direction that is opposite the first direction relative to the round element axis.

12. The SBT of claim 10, wherein the rotation of the front interface relative to the central stand includes a rotational displacement of the rear portion of the snowboard along to the slide rail of about 180 degrees and a tilt of the snowboard relative to a central axis in a range of about fifty degrees to about negative fifty degrees.

13. The SBT of claim 10, wherein:
the rear tilt interface further includes a rear rectangular portion;
the round contact element includes a central tube that is connected to the rear rectangular portion at a first end and configured to be connected to the snowboard at a second end; and
the round contact element includes an outer tube positioned over a portion of the central tube.

14. The SBT of claim 8, further comprising a return assist cord that includes a first end and a second end and is comprised of an elastic material, wherein:
the first end is configured to be attached to a rear portion of the snowboard;
the second end is attached to a bracket that is substantially aligned with a central position of the SBT; and
the return assist cord is configured to reduce weight on the rear portion of the snowboard that is imposed by a user and to help return the snowboard to the central position following rotational displacement of the snowboard from the central position.

15. The SBT of claim 8 further comprising:
an SBT platform; and
an adjustment plate that is connected to the SBT platform and the central stand, the adjustment plate configured to enable movement of the central stand relative to the slide rail to accommodate positioning of snowboards having multiple snowboard lengths.

16. A snowboard trainer (SBT), comprising:
an SBT platform;
a slide rail that extends from a first end to a second end;
three slide supports that support the slide rail relative to the SBT platform, wherein heights of the slide supports are adjustable;
a central stand positioned between the first end and the second end of the slide rail on the SBT platform;
a central board receiver that is connected to the central stand;
a rear interface that is configured to be secured to a rear portion of a snowboard;
a front interface that is configured to be secured to a front portion of the snowboard, the front interface including a roller bearing that is size to be retained in the central board receiver such that when the roller bearing is received in the central board receiver, the front interface three-dimensionally rotates relative to the central stand; and a return assist cord that includes a first end and a second end and is comprised of an elastic material, wherein the first end is configured to be attached to a rear portion of the snowboard; the second end is attached to a bracket that is substantially aligned with a central position of the SBT; and the return assist cord is configured to reduce weight on the rear portion of the snowboard imposed by a user and to help return the snowboard to the central position following rotational displacement of the snowboard from the central position, wherein the central stand is positioned relative to the slide rail such that when the front interface is secured to the snowboard and the roller bearing is retained in the central board receiver, the rear interface secured to the snowboard contacts an outer surface of the slide rail.

17. The SBT of claim 16, wherein the rear interface includes:

a rear tilt interface that includes a round contact element that contacts the outer surface of the slide rail to elevate the rear portion of the snowboard from the slide rail and enables rotation of at least the rear portion of the snowboard about a round element axis of the round contact element; and rear edge protectors that are positioned over portions of rear edges of the snowboard, the rear edge protectors being configured to reduce damage to the rear edges of the snowboard while allowing movement of the snowboard relative to the slide rail.

18. An SBT system comprising:

the SBT of claim 17;

a computing system implementing a training module and/or a game module; and one or more sensors that are configured to measure data indicative of a position of the snowboard relative to the front interface and the slide rail and to communicate the data to the computing system for use in the training module and/or a game module, wherein the computing system includes one or more processors and the training module and/or the game module include a non-transitory computer-readable medium having encoded therein programming code executable by the one or more processors to perform training or gaming operations based at least partially on the data.

* * * * *